US005298691A

United States Patent [19]

Leight

[11] Patent Number: 5,298,691

[45] Date of Patent: Mar. 29, 1994

[54] SOILING RESISTANT BANDED EARPLUG

[76] Inventor: Howard S. Leight, 4061 Glencoe Ave., Marina del Rey, Calif. 90292

[21] Appl. No.: 943,509

[22] Filed: Sep. 11, 1992

[51] Int. Cl.[5] .................... A61B 7/02

[52] U.S. Cl. .................... 181/135; 181/137

[58] Field of Search .................... 181/130, 131, 132, 133, 181/135, 136, 137, 128, 129; 128/152, 866; 381/25, 183, 187

[56] References Cited

U.S. PATENT DOCUMENTS

| | | | |
|---|---|---|---|
| 2,498,960 | 2/1950 | Mullin | 181/131 |
| 2,780,681 | 2/1957 | Shaper | 181/131 |
| 3,470,975 | 10/1969 | Haiken | 181/131 |
| 3,790,082 | 7/1976 | Leight | 128/152 |
| 4,554,993 | 11/1985 | Houng | 181/130 |
| 4,819,624 | 4/1989 | Leight et al. | 128/866 |
| 5,117,464 | 5/1992 | Jones et al. | 381/183 |

*Primary Examiner*—Michael L. Gellner
*Assistant Examiner*—Khanh Dang
*Attorney, Agent, or Firm*—Arthur Freilich; Robert D. Hornbaker; Leon D. Rosen

[57] ABSTRACT

A band earplug apparatus is described, of the type which includes a pair of earplug devices (20, 22) lying on the ends of a band (12) that fits halfway about a person's head, which avoids soiling of the earplug devices when the band is laid on a dirty surface. The band is designed so its middle portion (24) rests stably on a horizontal surface (5), and with the end portions then extending at an incline (A) away from the horizontal surface to hold the ends (14, 16) of the band and the earplug devices (20, 22) thereon spaced from the horizontal surface.

4 Claims, 1 Drawing Sheet

SOILING RESISTANT BANDED EARPLUG

BACKGROUND OF THE INVENTION

One type of earplug apparatus includes a resilient band that fits halfway about the head of the wearer and which has opposite ends holding earplug devices that press against the wearer's ears. Such banded earplugs are used in large numbers in manufacturing and other industries to protect against loud noises. When a worker removes a banded earplug, he often lays it on a nearby horizontal surface such as that of a table, shelf, or desk. The horizontal surface may be soiled from dust, grease, or other contaminants in the environment, and may soil the earplug devices that touch them. This can lead to dirtying the worker's ears or to the worker often requiring a new clean banded earplug. A banded earplug which reduced soiling of the earplug devices, would be of considerable value.

SUMMARY OF THE INVENTION

In accordance with one embodiment of the present invention, a banded earplug is provided which avoids soiling of its earplug devices when the banded earplug is laid on a largely horizontal surface. The banded earplug includes a band having a middle portion formed to rest stably on a horizontal surface, and having end portions that extend away from the horizontal surface. The earplug devices are mounted at locations on the end portions furthest from the middle portion, so they are held away from the horizontal surface to avoid soiling. The middle portion of the band can form intermediate portions that each includes a pair of spaced bearing locations that rest on the horizontal surface and a raised portion between the bearing locations. The raised portion helps assure stable resting of the earplug even on an uneven largely horizontal surface.

The novel features of the invention are set forth with particularity in the appended claims. The invention will be best understood from the following description when read in conjunction with the accompanying drawings.

DESCRIPTION OF THE PREFERRED EMBODIMENT

Figure 1:
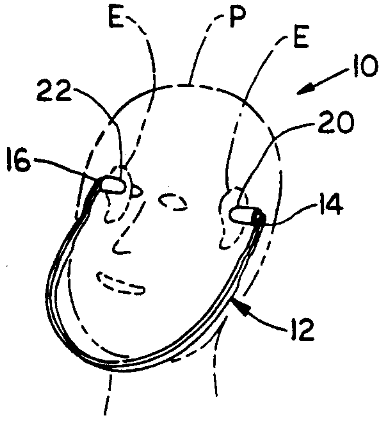
FIG. 1 is an isometric view of a banded earplug apparatus of the present invention, showing it worn by a person.

FIG. 1 illustrates a banded earplug 10 which includes a resilient band 12 designed to extend about halfway around the head of a person P, and which has opposite ends 14, 16 that lie opposite the ears E of the person. A pair of earplug devices 20, 22 are each attached to a different one of the band ends. The resilient band 12 urges the earplug devices 20, 22 towards the person's ears, so each device presses against the entrance to the ear canal of the person, to form a seal which minimizes the passage of noise to the person's ear.

Banded earplugs of this general type are well known, and are commonly used in workplaces such as factories, where they are reused many times before disposal. Workers commonly remove the earplugs for extended periods such as during coffee and lunch breaks, when the banded earplugs must be stored. Such storage is commonly achieved by merely laying the banded earplug on an easily available surface such as an unused region of a table. Since surfaces in manufacturing plants often become dirty from oil, bits of metal that have been ground or machined from work pieces, and other soiling material, the earplug devices often become soiled. If a workman places a soiled earplug against his ears, the soiling material may harm the worker, or at least feel uncomfortable. The alternative is for the worker to request another banded earplug, which results in additional expense.

Figure 3:
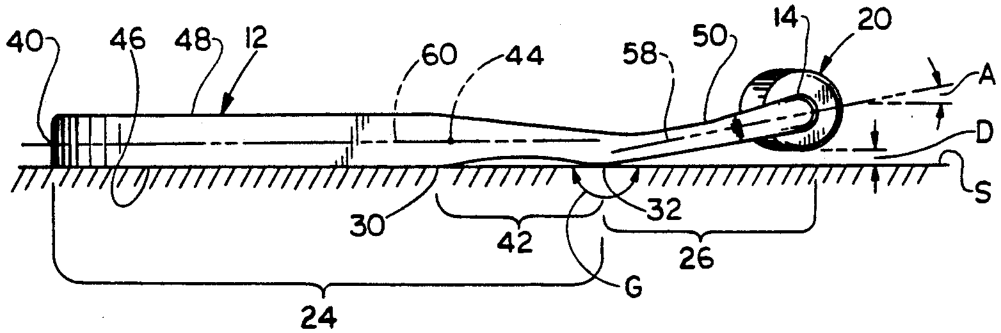
FIG. 3 is a view taken on the line 3—3 of FIG. 2.

In accordance with the present invention, the banded earplug 10 is constructed so that when laid on a largely flat and horizontal surface S such as shown in FIG. 3, the earplug devices such as 20 are held away from the surface, to thereby avoid soiling of the earplug devices when the horizontal surface S is dirty. The band 12 includes a middle portion 24 and opposite end portions 26, 28. The middle portion 24 is designed to rest stably on the surface S, with the end portions extending at an incline angle A. The incline brings the band ends 14, 16 sufficiently away from the surface S to hold the earplug devices spaced a distance D away from the surface.

The middle portion of the band includes a pair of bearing locations 30, 32 and 34, 36 which are designed to rest on a horizontal surface. Each pair of bearing locations includes an inner bearing location such as 30 closest to the center 40 of the middle portion 24 of the band, and a second or outer bearing location such as 32 furthest from the center 40. The band has an imaginary centerline 60 which passes through the center 40 and which lies halfway between the earplug devices 20, 22. The band middle portion also preferably includes a recessed or raised portion 42 extending between each pair of bearing locations 30, 32. The raised portion 42 helps assure that the band will lie stably on a surface with the band ends 14, 16 far enough from the surface to avoid contact of the earplug devices with the surface, even if the surface has moderate irregularities. The center of gravity of the banded earplug is at the location 44 which is preferably located closer to the inner bearing location 30 than to the outer one 32, and which is generally located at about the inner location 30. It can be seen that bearing location 30 lies closer to the center of gravity 44 than either the band middle 40 or the earplug devices such as 20, as seen in the side view of FIG. 3. It also can be seen that the length of the inclined end portion 26 is more than 10% of the entire length (portion 24 plus portion 26) of the band as seen in the side view of FIG. 3.

The band has lower and upper faces 46, 48 and it is fairly obvious to the worker which face 46 is to be laid on the surface to avoid soiling of the earplug devices. Instructions provided with each banded earplug point this out to the worker. The worker can be encouraged to grasp the banded earplug at the end portions such as 26 near the inclined regions 50, to facilitate lay-down of the banded earplug on a surface.

Figure 2:
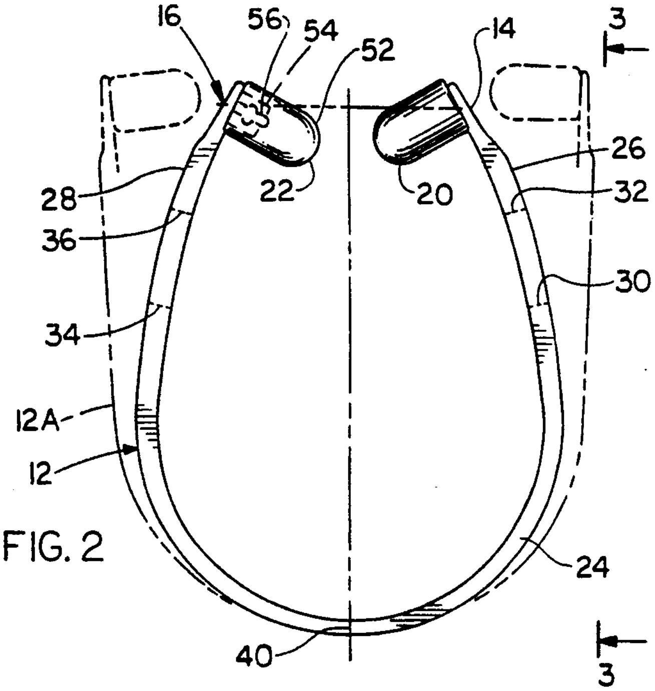
FIG. 2 is a plan view of the band earplug apparatus of FIG. 1.

In one banded earplug design by applicant, each earplug device such as 22 shown in FIG. 2, includes an earplug body 52 of slow recovery foam material, of a diameter of about 18 mm so that it presses and seals against the entrance to the ear canal without substantially entering the ear canal. The body 52 is held on a foam armature 54 anchored by a post 56 molded integrally with the end 16 of the band. The band has to be spread apart to the configuration 12A to fit around the person's head, and then applies a force of about 6 ozs. to the ears of the person. As shown in FIG. 3, the band end portions such as 26, extend along an imaginary line 58 angled at an angle A of about 11° from the length of the middle portion of the earplug, as indicated by an imaginary line at 60, and from the horizontal plane of the horizontal surface S. It is noted that FIG. 3 is taken perpendicular to the centerline 60 and along the plane of the horizontal surface S. Applicant prefers to maintain the angle A less than about 45°, because a large angle results in an earplug of somewhat greater bulk and therefore somewhat greater expense, and because a small angle is sufficient to keep the devices away from the horizontal surface and has a largely straight aesthetic appearance. The angle A is generally at least 10°.

Figure 4:
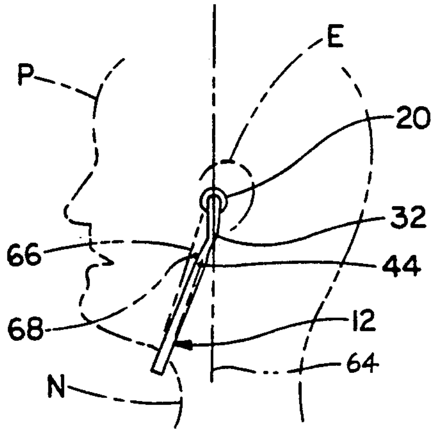
FIG. 4 is a side elevation view of the apparatus of FIG. 1, worn on the person.

The construction of the band, with the end portions such as 26 angled from the middle portion 24, also aids in comfortable wearing of the band earplug. As shown in FIG. 4, the banded earplug is preferably worn with the convex side (i.e., forming an angle G of over 180°) at location 32 facing rearwardly. This results in the center of gravity 44 of the band earplug (as seen in the side views of FIGS. 3 and 4) lying closer to a vertical line 64 passing through the earplugs such as 20. This may be compared to a straight band indicated at 66 where the center of gravity 68 lies further from the vertical line. As a result, in the present band 12 there is less gravity-caused movement tending to pivot the banded earplug more toward the vertical (wherein the center of gravity 44 lies on line 64), and the banded earplug is less likely to slip and press against the neck N of the wearer and discomfort him. The distance between the centers of gravity 44 and 68 increases as the tilt angle A increases.

Thus, the invention provides a band earplug apparatus or banded earplug which avoids soiling of the earplug devices that press against the wearer's ears, when the banded earplug is laid on a largely horizontal surface for storage. The banded earplug includes a band with a middle portion formed to rest stably on a flat horizontal surface and end portions that extend at an angle to the middle portion to hold the earplug devices away from the support surface. The middle portion can be formed with pairs of bearing locations that normally rest on a horizontal surface and can be formed with a recessed or raised portion between the bearing locations, to help avoid unwanted tilting of the earplug if there is a bump on the support surface under the raised portion of the band. The end portions of the band preferably extend at a small to moderate incline from a horizontal surface on which the middle portion of the band rests.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. A noise-blocking band earplug apparatus for use in a noisy and dirty environment, comprising:

a band which can extend about halfway around a person's head, and which has opposite ends that can lie opposite the ears of the person and a middle lying halfway between said ends along said band;

a pair of earplug devices, each attached to a different one of said band ends, said band being resilient in movement of said band ends toward and away from each other and being constructed to urge said band ends and the earplug devices thereon toward the person's ears, and said earplug devices extending from said band ends toward each other and being constructed to block noise from entering the person's ear canal;

said band having an imaginary centerline which lies halfway between said earplug devices and passes through said band middle, and said band having a middle portion formed to rest stably on a flat horizontal surface which lies in a horizontal plane, and said band having end portions that extend generally away from said middle as seen in a plan view when said band rests on a horizontal surface, said end portions each having a length (26) that is more than 10% of the horizontal length (26 plus 24) of the earplug and said end portions each extending at an upward incline of at least about 10° away from said horizontal surface as seen in a side view taken in the plane of said horizontal surface and perpendicular to said imaginary centerline, to hold said band ends and said earplug devices thereon away from said surface, whereby to avoid soiling of said earplug devices when said horizontal surface is dirty.

2. The apparatus described in claim 1 wherein:

said band middle portion includes a center lying halfway between said ends along said band, and two pairs of bearing locations, each pair of bearing locations lying between said center and one of said end portions and engaging said horizontal surface, and said band having a concave portion raised from said horizontal surface, between said bearing locations, said band and earplug devices thereon having a predetermined center of gravity, and a first of said bearing locations lies closer to said center of gravity than to either said band middle of said earplug devices as seen in said side view.

3. A noise-blocking band earplug apparatus, for use in a noisy and dirty environment, comprising:

a band (12) which can extend about halfway around a person's head, and which has opposite ends that can lie opposite the ears of the person;

a pair of earplug devices (20, 22), each attached to a different one of said band ends, and said band being constructed to urge said band ends and the earplug devices thereon toward the person's ears;

said band having a middle portion (24) extending generally along an imaginary line (60) as viewed in a side view, and having end portions (26, 28) that each extends at an angle (A) of at least 10° away from said imaginary line (60) with each end portion having a length (26) of more than 10% of the band length (24 plus 26) as seen in a side view, said middle and end portions having a convex location (at 32) where they meet, whereby to help keep the band away from the wearer's neck when the apparatus is worn with said convex location facing rearwardly of the wearer.

4. In a noise-blocking band earplug which includes a band that fits about halfway around the head of a wearer and that has opposite end portions with ends holding earplug assemblies that extend toward each other when the band ends are spread apart and that press against the wearer's ears, the improvement wherein:

said band has a center and a pair of opposite end portions, and has a pair of bearing locations between said center and each of said end portions, each pair of bearing locations positioned to stably rest on a support surface which lies in a horizontal plane, and when said band is viewed in a side elevation view in which said earplug assemblies lie one behind the other, said end portions each generally extending at an upward incline substantially form one of said bearing locations, each end portion having an end furthest from said bearing locations, each earplug assembly mounted on one of said ends, and when seen in said side elevation view said end portions are inclined at least on the order of 10° to hold the corresponding earplug assembly spaced above said support surface;

each of said pairs of bearing locations includes first and second locations respectively closest to and furthest from said band center, said band having a raised concave region between each of said first and second bearing locations, said raised region lying above said support surface when said bearing locations lie thereon.

* * * * *